US006600326B2

(12) United States Patent
Weiss

(10) Patent No.: US 6,600,326 B2
(45) Date of Patent: *Jul. 29, 2003

(54) VOLTAGE APPLICATOR FOR TIRE INSPECTION AND METHOD

(76) Inventor: Arnold A. Weiss, 8777 Walton Oaks Dr., Bloomington, MN (US) 55438

( * ) Notice: Subject to any disclaimer, the term of this patent is extended or adjusted under 35 U.S.C. 154(b) by 0 days.

This patent is subject to a terminal disclaimer.

(21) Appl. No.: 09/955,271

(22) Filed: Sep. 18, 2001

(65) Prior Publication Data

US 2002/0011849 A1 Jan. 31, 2002

Related U.S. Application Data

(63) Continuation of application No. 09/425,574, filed on Oct. 22, 1999, now Pat. No. 6,304,090.

(51) Int. Cl.⁷ ............. G01N 27/00; G01R 31/08; H01H 9/50; G01M 17/02
(52) U.S. Cl. ............. 324/558; 324/516; 324/517; 324/518; 324/536; 73/146
(58) Field of Search ................ 324/558, 516, 324/517, 518, 536, 691, 693, 701; 73/146, 146.5

(56) References Cited

U.S. PATENT DOCUMENTS

| | | | |
|---|---|---|---|
| 1,779,907 A | 10/1930 | Dye | |
| 2,345,679 A | 4/1944 | Linse | |
| 2,378,237 A | 6/1945 | Morris | |
| 2,503,992 A | 4/1950 | Becker | |
| 2,612,772 A | 10/1952 | McConnell | |
| 2,753,521 A | 7/1956 | Abrams | |
| 2,940,305 A | 6/1960 | Williams | |
| 2,941,144 A | 6/1960 | Cannon | |
| 3,056,286 A | 10/1962 | Gibson | |
| 3,148,535 A | 9/1964 | Lemelson | |
| 3,228,232 A | 1/1966 | Proctor | |
| 3,238,767 A | 3/1966 | Clynes | |
| 3,285,059 A | 11/1966 | Bogle | |
| 3,336,794 A | 8/1967 | Wysoczanski | |
| 3,350,924 A | 11/1967 | King | |
| 3,354,700 A | 11/1967 | Schindler | |
| 3,367,173 A | 2/1968 | Uphoff | |
| 3,371,524 A | 3/1968 | Wloszek | |
| 3,384,733 A | 5/1968 | Burbank | |
| 3,456,495 A | 7/1969 | Stinger | |
| 3,465,242 A | 9/1969 | Gruetzmacher et al. | ...... 324/54 |
| 3,552,190 A | 1/1971 | Lefebvre | |
| 3,558,889 A | 1/1971 | Weighart | |
| 3,576,126 A | 4/1971 | Weighart | |
| 3,593,120 A | 7/1971 | Mandula | |
| 3,604,249 A | 9/1971 | Wilson | |
| 3,631,849 A | 1/1972 | Norris | |
| 3,646,805 A | 3/1972 | Walters | |
| 3,665,754 A | 5/1972 | Krautkramer | |
| 3,670,562 A | 6/1972 | Muto | |
| 3,712,119 A | 1/1973 | Cross | |
| 3,780,570 A | 12/1973 | Collins | |
| 3,786,673 A | 1/1974 | Weissmann | |

(List continued on next page.)

Primary Examiner—Christine Oda
Assistant Examiner—Anjan K. Deb
(74) Attorney, Agent, or Firm—Patterson, Thuente, Skaar & Christensen, P.A.

(57) ABSTRACT

An apparatus for detecting flaws in a tire. The apparatus may contain a frame sized to be placed in the interior of the tire, at least one device operably connected to the frame so that upon rotation of the tire the frame travels around the interior of the tire, where the frame is substantially supported by the tire, and at least one pin attached to the frame, where the at least one pin is adapted to be connected to a voltage generator to create an electric field near the surface of the tire when in use so that an electric arc is produced upon the presence of a flaw in the tire.

25 Claims, 7 Drawing Sheets

U.S. PATENT DOCUMENTS

| | | |
|---|---|---|
| 3,794,964 A | 2/1974 | Katakura |
| 3,812,708 A | 5/1974 | Cowan |
| 3,815,407 A | 6/1974 | Lavery |
| 3,871,210 A | 3/1975 | Himmler |
| 3,872,715 A | 3/1975 | Pittaro |
| 3,882,717 A | 5/1975 | McCauley |
| 3,918,025 A | 11/1975 | Koshikawa |
| 3,967,498 A | 7/1976 | Pezzillo |
| 3,978,712 A | 9/1976 | Cowan |
| 3,981,184 A | 9/1976 | Matay |
| 4,059,989 A | 11/1977 | Halsey |
| 4,065,958 A | 1/1978 | Krylova |
| 4,083,232 A | 4/1978 | Heyser |
| 4,088,028 A | 5/1978 | Hildebrandt |
| 4,089,225 A | 5/1978 | Kraska |
| 4,089,226 A | 5/1978 | Kraska |
| 4,117,733 A | 10/1978 | Gugel |
| 4,274,289 A | 6/1981 | Weiss |
| 4,279,157 A | 7/1981 | Schomberg |
| 4,285,235 A | 8/1981 | Dugger |
| 4,297,876 A | 11/1981 | Weiss |
| 4,327,579 A | 5/1982 | Weiss |
| 4,337,660 A | 7/1982 | Weiss |
| 4,365,514 A | 12/1982 | Ho |
| 4,372,366 A | 2/1983 | Dugger |
| 4,516,068 A | 5/1985 | Hawkinson |
| 4,520,307 A | 5/1985 | Weiss |
| 6,050,136 A | 4/2000 | Hawkinson |
| 6,304,090 B1 * | 10/2001 | Weiss ......................... 324/516 |

* cited by examiner

VOLTAGE APPLICATOR FOR TIRE INSPECTION AND METHOD

This is a Continuation of application Ser. No. 09/425,574 filed Oct. 22, 1999 now U.S. Pat. No. 6,304,090.

BACKGROUND OF THE INVENTION

1. Field of the Invention

This invention relates to devices and methods for testing tires for flaws. More particularly, this invention relates to a high voltage device and method for testing for flaws in a tire.

2. Background Information

In the tire retread industry, visual testing is performed on used tire carcasses to ensure that they are free from cuts, holes, and nails. In this regard, it is essential that the testing be accomplished in a minimum of time, yet with reliability so as to ensure that all defective carcasses are culled. The cuts and holes of culled carcasses can then be patched and the nails removed, prior to buffing and retreading. (Note, this is from Weiss et al U.S. Pat. No. 4,520,307 (column 1, lines 14–21) which was incorporated by reference.)

Visual inspection and testing of tires is a common practice in the tire retread business. Testing of used tires for flaws, such as gashes, holes, and nails and other foreign objects, is a common practice. After detection, the nails or other objects may be removed and/or the tire may be patched in order to repair the tire. Although visual inspection may be used to detect some flaws, other flaws may not be visible to the human eye or may not be detected by visual inspection due to human error.

Some devices do exist for the detection of flaws in tires. For example, some machines may inflate the tire and then detect flaws either ultrasonically or by observing bubbles that indicate escaping air. Such machines, however, have the disadvantage of requiring inflation of the tire to be tested.

Other devices use high voltage to detect flaws in tires. See U.S. Pat. No. 4,520,307 ('307 patent), issued to Weiss on May 28, 1985. The '307 patent describes a high voltage inspection system in which a high voltage head 4 is mounted within the tire. A tire spreader (with arms 22) is used to spread the beads of the tire apart and the high voltage head 4 is then mounted within the tire. '307 patent, FIG. 4; Col. 5, ll. 20–28, 44–48. A rotating drive mechanism 16 with drive rollers 18 and 20 is then used to rotate the tire. '307 patent, FIG. 4; Col. 4, ll. 65 to Col. 5, ll. 3. Upon detection of a flaw, an arc-over develops as current flows through the head 4 to a reference head on the other side of the tire, which may be the rollers 18, 20. '307 patent, Col. 5, ll. 65 to Col. 6, ll. 4. The operator may then stop the rotation of the tire and mark the flaw with a pen or crayon so it may be fixed at a later time.

The device of the '307 patent requires the use of a "suitable mechanical linkage 25" to position the head 4 within the tire. '307 patent, Col. 5, ll. 44–48. Tire testing devices developed in accordance with the teachings of the '307 patent may have somewhat complex mounting arms for the head because positioning of the head 4 within the tire is important for a number of reasons. The head must be sized to be small enough to fit within the beads of the tire when spread, and yet the head should be large enough to create an electric field over the desired surface of the tire to be tested. Pins or small chains may be used to carry an electric charge on the head and, in that case, the pins should cover the surface area of the tire to be tested. Alignment of the head within the tire becomes key so that the pins are properly spaced throughout the inside of the tire.

Pneumatic and mechanical arms are commonly used as a mechanical link to mount the head within the tire during testing. Such pneumatic and mechanical arms typically allow for the head to be moved vertically as well as horizontally. Using such a pneumatic and/or mechanical arm, the head may be placed within the tire so that testing using high voltage may be carried out.

Such pneumatic and/or mechanical arms for the placement of a head within the tire have a number of disadvantages. One disadvantage of such arms is expense. A complex arm that allows for precise placement of the head within the tire may be costly and may significantly affect the overall cost of the tire tester. In addition, such pneumatic and/or mechanical arms may require a large amount of time to properly place within the tire. There are, for example, a large variety of adjustments that may be made with such arms to properly adjust the head within the tire to be tested. A large number of different mechanical or pneumatic arms may also be necessary for different tire sizes. Finally, it may be difficult to achieve the proper placement of the head within the tire, which may affect the performance of the tire tester. The overall cost of prior art tire testing devices may also be high due to the large number of pieces of machinery required for use of such systems, such as a rotating apparatus for the tire and a spreader for the tire.

Because the mechanical or pneumatic arm used to place the head within the tire is typically mounted to a specific tire spreader, and because tire spreaders may come in a variety of designs, the mechanical or pneumatic arms commonly have to be built specifically for one tire spreader size and design. Prior art testing devices that use a mechanical or pneumatic arm to place the head within the tire are therefore specifically designed for a tire spreader and are therefore dependent on the configuration of the tire spreader. Such testing systems, in fact, typically are purchased along with a specific tire spreader, which results in an expensive tire tester.

A need exists for a tire testing device that has a cost efficient design, that allows a head carrying voltage to be properly placed and centered within a tire, and that may be placed within a tire and properly centered quickly and easily. A need also exists for a tire testing device that is independent of the configuration of the tire spreader and that may therefore be sold separately from a tire spreader, which reduces the price of the tire testing device.

SUMMARY

One embodiment of the invention is an apparatus for detecting flaws in a tire. In this embodiment, the apparatus may contain a frame sized to be placed in the interior of the tire, at least one device operably connected to the frame so that upon rotation of the tire the frame travels around the interior of the tire, wherein the frame is substantially supported by the tire, and at least one pin attached to the frame, wherein the at least one pin is adapted to be connected to a voltage generator to create an electric field therein and near the surface of the tire when in use so that an electric arc is produced upon the presence of a flaw in the tire. In this embodiment, the at least one device may cause the frame to self-center within the tire upon rotation of the tire.

Another embodiment of the invention also comprises an apparatus for detecting flaws in a tire. In this embodiment, the invention contains a frame sized to be placed in the interior of the tire, a rolling device operably connected to the frame so that upon rotation of the tire the frame travels around the interior of the tire and the weight of the frame keeps the frame near a bottom interior portion of the tire, and a pin attached to the frame, wherein the pin is adapted to be connected to a voltage generator to create an electric field therein and near the surface of the tire when in use so that an electric arc is produced upon the presence of a flaw in the tire.

An advantage of the present invention as described above is that it is simple and easy to use in that it may be quickly and easily centered within a tire during use. In addition, the present invention may be cheaper than prior art testing systems because a pneumatic and/or mechanical arm is not needed to precisely place the head within the tire. Further, the invention is a simple design that it is not overly complex, so it takes up less space in a tire retread shop than prior art tire testers.

Another embodiment of the invention is a system for detecting flaws in a tire. In this embodiment, the system may contain a frame sized to be placed in the interior of the tire, at least one device operably connected to the frame so that upon rotation of the tire the frame travels around the interior of the tire, wherein the frame is substantially supported by the tire, a high voltage generator, and a plurality of pins attached to the frame, wherein the voltage generator is connected to the pins to produce an electric field therein so that an electric arc is produced upon detection of a flaw in the tire. This embodiment of the invention may also contain a circuit containing a current meter to measure the current through the plurality of pins, wherein the circuit stops rotation of the tire upon measuring a jump in current which indicates a flaw in the tire.

This embodiment of the invention has advantages of cost, ease of use, and decreased complexity over the prior art.

Yet another embodiment of the invention is a method for detecting flaws in a tire. In one embodiment, the method comprises the acts of placing a frame in the interior of the tire, wherein the frame has at least one roller attached thereto, applying an electric field to the inside of the tire through the frame, and rotating the tire so that the frame rotates on the at least one roller around the interior of the tire, wherein an electric arc is produced upon detection of a flaw in the tire.

Much like the embodiments above, this embodiment has the advantages of cost, ease of operation, and decreased complexity compared to prior art tire testing devices.

Other features and advantages of the tire testing device of the present invention will become more fully apparent and understood with reference to the following description and drawings, and the appended claims.

DETAILED DESCRIPTION

The accompanying Figures depict embodiments of the tire tester of the present invention, and features and components thereof. With regard to means for fastening, mounting, attaching or connecting components of the present invention to form the invention as a whole, unless specifically described otherwise, such means are intended to encompass conventional fasteners such as machine screws, machine threads, seals, snap rings, clamps, rivets, nuts and bolts, toggles, pins and the like. Components may also be connected adhesively, by friction fitting, or by welding or deformation, if appropriate. Unless specifically otherwise disclosed or taught, materials for making components of the present invention are selected from appropriate materials such as metal, metallic alloys, natural or synthetic materials, plastics and the like, either rigid or soft, and appropriate manufacturing or production methods including casting, extruding, molding and machining may be used.

Any references to front and back, right and left, top and bottom, upper and lower, and horizontal and vertical are intended for convenience of description, not to limit the present invention or its components to any one positional or spacial orientation. All dimensions of the components in the attached Figures may vary with a potential design and the intended use of an embodiment of the invention without departing from the scope of the invention.

A. General Overview

Figure 1:
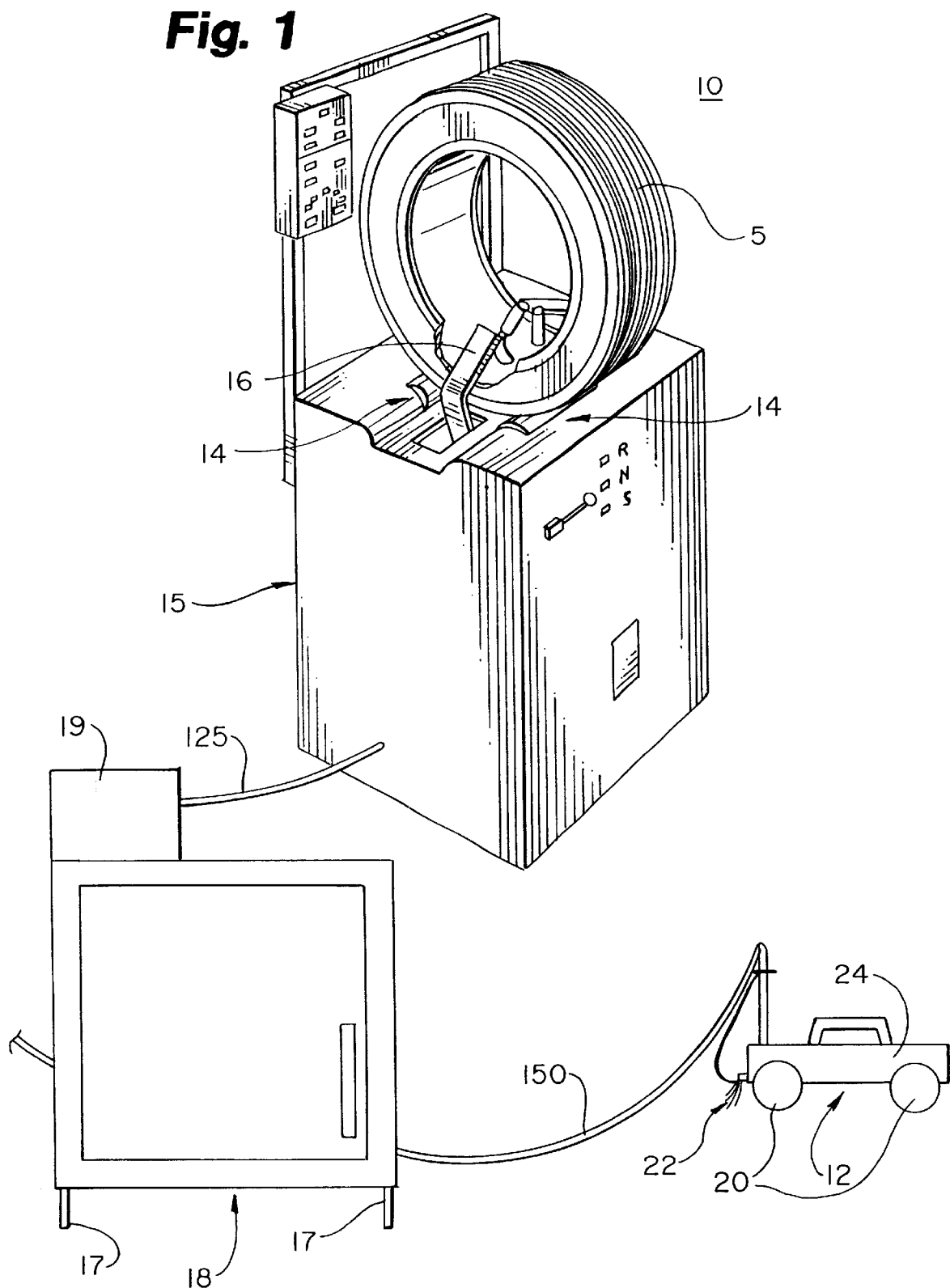
FIG. 1 is a view of one embodiment of the invention including a frame, a voltage generator, and a motor for rotating a tire that is to be tested.

A number of embodiments of the invention are shown in FIGS. 1–7. FIG. 1 shows the tire tester 10 of the invention. The tire tester 10 generally comprises a frame 12 and a voltage generator 18. The frame 12 may contain at least one rolling device 20 and at least one pin 22. In operation, the tire tester 10 may use a device for rotating a tire 5, such as rollers 14 connected to any variety of motor 15 that rotates the rollers 14. In addition, a tire spreader may be used to spread the beads of the tire 5 apart to make it easy to reach the interior of the tire 5. Typically, such tire spreaders and rotating devices cause the tire to rotate about a substantially horizontal axis. FIG. 1 shows two spreader arms 16 which may be used to spread the beads of the tire 5. Although a tire spreader is not necessary for operation of the invention, it may make use of the invention easier. One suitable tire spreader and rotating device is manufactured by Branick Industries of Fargo, N. Dak. Tire spreaders and rotating machines are commonly used in tire retread shops for visual inspection (without high voltage) of tires 5. The user may simply visually inspect the inside or outside of the tire 5 as it rotates using a tire spreader and rotating machine.

In operation, the frame 12 may be placed in the interior of the tire 5 after the tire 5 has been placed on the rotating device, and, optionally, after the beads of the tire 5 have been spread using the spreader arms 16. The voltage generator 18 may be connected to the frame 12 so as to create an electric field in the pin 22 near the frame 12. When the tire 5 is rotated using the rotating device or motor 15, the frame 12 rolls on its rolling device 20 so as to remain in substantially the same position within the tire 5. The inside of the tire 5, therefore, moves with respect to the frame 12, such that a given point on the interior surface of the tire 5 will eventually travel in a full circle with respect to the frame 12.

Because the voltage generator 18 creates an electric field near the interior surface of the tire 5, an electric arc will connect the frame to a conductor, such as the rollers 14, upon detection of a flaw in the tire 5. The tire 5, and particularly the inside surface, is a good insulator, and upon detection of a flaw (a hole in the tire 5 or a nail or other object), current will flow from the pins 22 of the frame 12 to the rollers 14, and this current will be visible as an electric arc or a spark. If a tire 5 with steel in the interior is being tested, the steel serves as a reference and current flows from the pins 22 to the steel in the tire 5 and an electric arc will be present. The user of the tire tester 10 may view this electric arc, recognize that it indicates a flaw in the tire 5, stop rotation of the tire 5, and then mark the flaw so that it may be mended at a later time. Rotation of the tire 5 may then be resumed until the entire interior surface of the tire 5 has been tested for flaws.

1. The Voltage Generator and Current Meter

A voltage generator 18 may be used to impart a voltage to the frame 12 or a portion thereof. In one embodiment, the voltage generator 18 may be used to generate a high voltage, such that the electric arcs produced upon detection of a flaw are visible to a human eye. In one embodiment, therefore, the voltage generator 18 may produce a voltage of approximately 40,000 volts. In other embodiments, voltages of from 20,000 to 60,000 volts may be used. Any voltage, including those within and outside the range of the voltages listed herein, may be used within the scope of the tire tester 10 of the invention. The voltage generator 18 shown in FIG. 2 may be contained within a box with wheels 17 such that it may be easily moved in a tire retread shop to different areas. U.S. Pat. No. 4,520,307, which is hereby incorporated in its entirety by reference into this specification, discloses one voltage generator 18 that is suitable for use in connection with the invention. Other voltage generators, and in particular other high voltage generators, may also be used within the scope of the invention.

A current meter 19 may be used with the tire tester 10 of the invention in one embodiment to measure the current passing through the pins 22 and therefore through the tire 5 upon the detection of a flaw. The current meter 19, which may be a typical ammeter and/or current transformer or other known device used to detect, measure, or sense current, may therefore be connected to the motor 15 driving the rollers 14 with a cord 125. In use, the current meter 19 may also be connected to the frame 12, and more particularly to the pins 22, such that the current meter 19 may measure the current passing there through. FIG. 1 illustrates a connection of the current meter 19 to the voltage generator 18 and, through the voltage generator 18 to the frame 12.

In operation, little or no current passes through the pins 22 and therefore the current meter 19 when the tire 5 acts as an insulator so that current does not flow through the tire 5. When a flaw is detected in the tire 5, however, current flows through the pins 22 and therefore the current meter 19 and also through the tire 5 to the rollers 14 or other reference source, and the current meter 19 may measure the current. Upon detection of a flaw, therefore, the current meter 19 may send a signal through the cord 125 to the motor 15 to cease rotation of the tire 5. Such "stop circuitry" that may be used within the scope of the invention is disclosed in U.S. Pat. No. 4,520,307, which is incorporated in its entirety by reference into this specification. Other circuitry, however, may also be used within the scope of the invention to measure the current through the pins 22 or through a similar reference point and to stop rotation of the tire 5 upon measurement of an appropriate current. In an embodiment in which a current meter 19 is used, flaws may be detected both visually by the user and electronically through use of the "stop circuitry." After the "stop circuitry" stops the rotation of the tire 5 upon detection of a flaw, and after the flaw has been marked by the user, the motor 15 may be started so that rotation of the tire 5 resumes and other flaws may be detected.

2. The Frame

Figure 2:
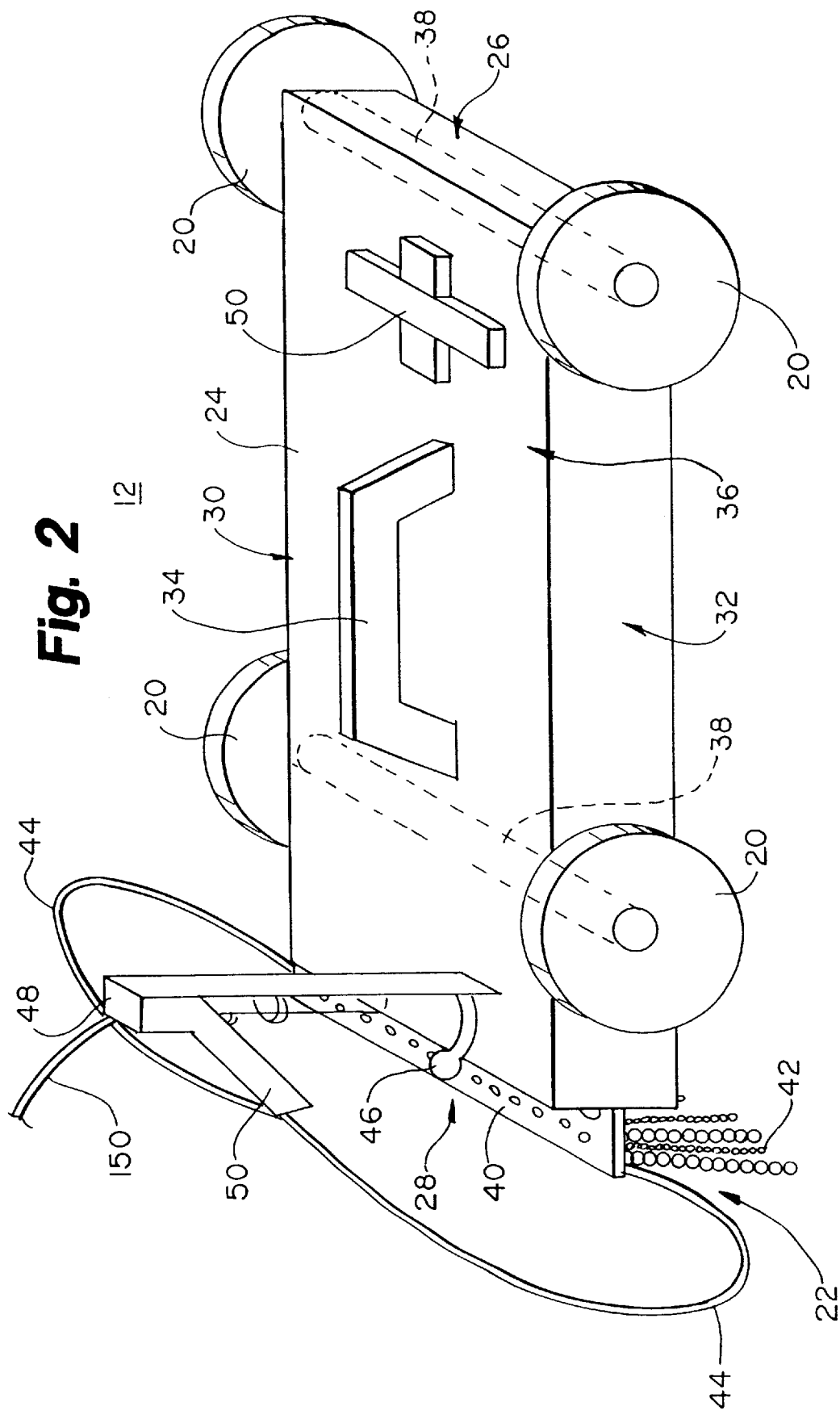
FIG. 2 is a side perspective view of the frame of the invention.
Figure 3:
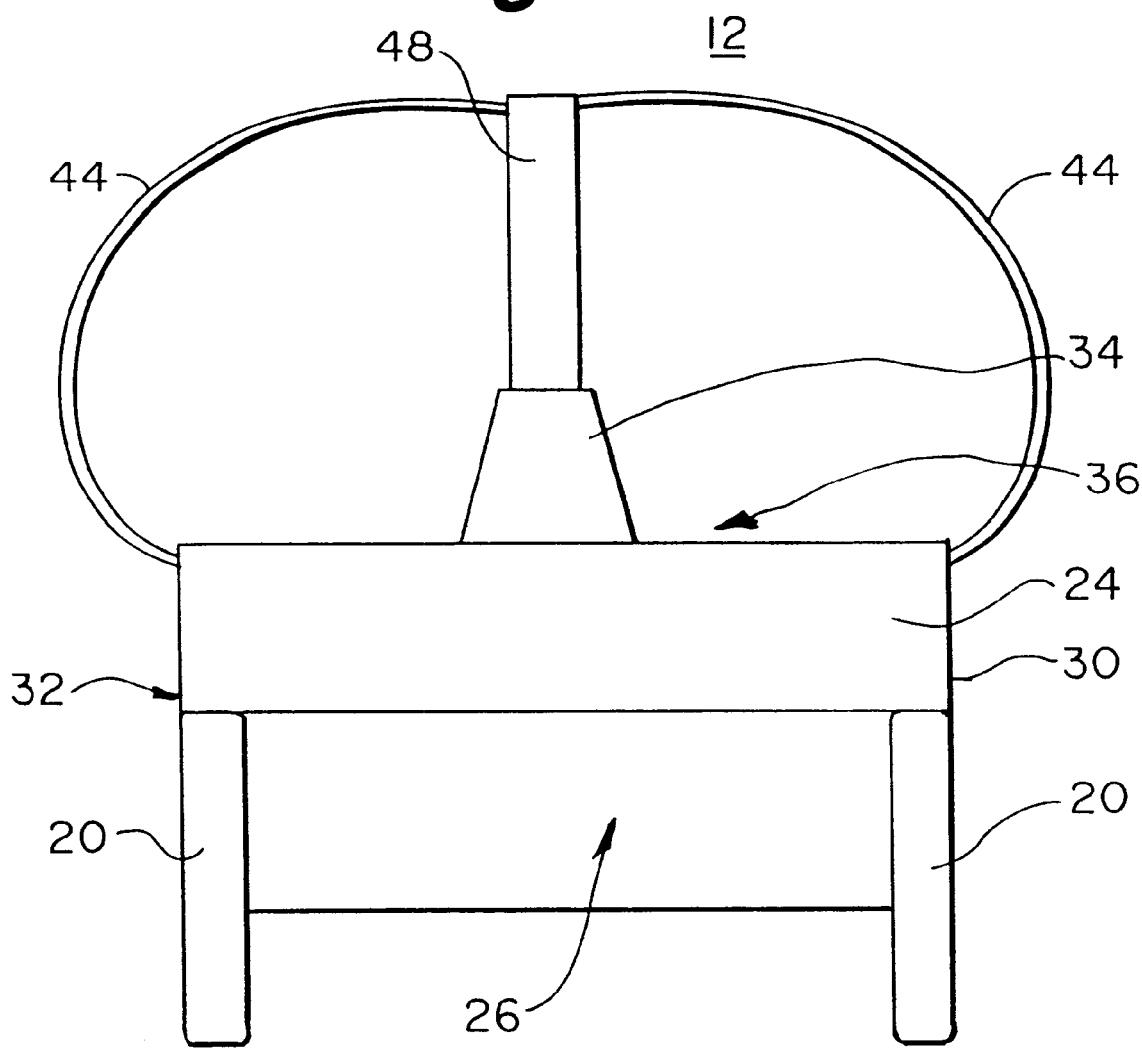
FIG. 3 is a front view of a second embodiment of the frame of the invention.
Figure 4:
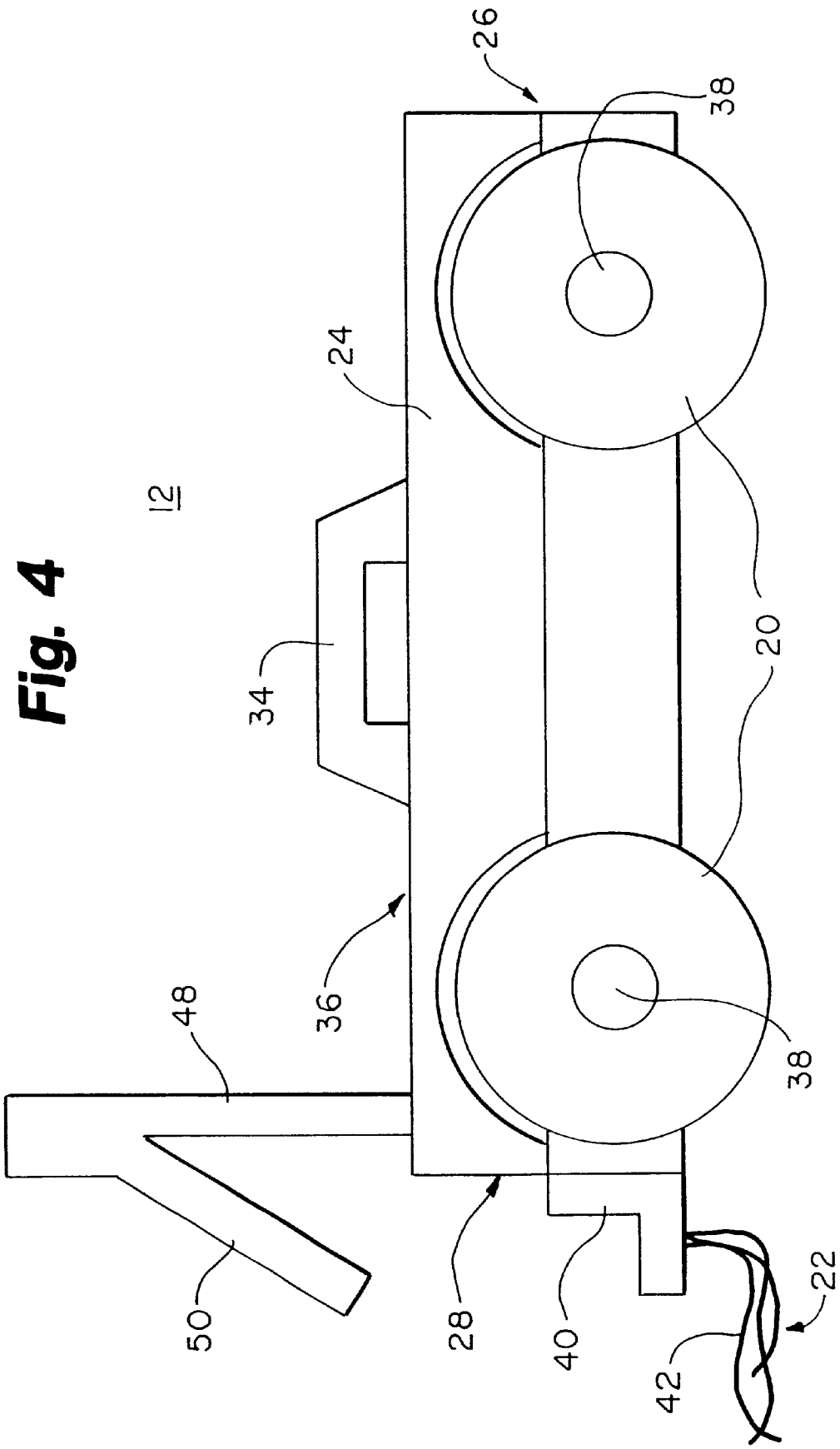
FIG. 4 is a side view of the embodiment of the frame of FIG. 3.

In one embodiment, the frame 12 may contain at least one device 20, at least one pin 22, and a body 24. FIGS. 2 through 4 show various views of embodiments of a frame 12 that may be used within the scope of the invention. The device 20 may be a rolling device 20 as depicted in the Figures, but the device may also be any device that allows the frame 12 to travel around the interior of the tire upon rotation of the tire. The device 20, therefore, may be lubrication on the frame 12, or wheels, or other rolling devices. FIG. 2 shows a perspective view of a frame 12 that may be used with the invention. The body 24 of the frame 12 may be of virtually any geometry. The body 24 illustrated in FIG. 2 is a simple rectangular block. Although such a rectangular block is depicted in FIG. 2, the body 24 could be configured as a square, an oval, or in some other geometry. Although symmetry between the front end 26 and the back end 28 and between a first side 30 and a second side 32 of the body 24 may be desirable, such symmetry is not required for the body 24. An even weight distribution of the body 24 may aid in keeping the body 24 balanced upon rotation of the tire 5, and such balance may aid in the centering of the frame 12 in the tire 5 upon rotation of the tire 5.

The size of the body 24 may vary depending on a number of factors, including the size of the tire 5 to be tested with the particular frame 12. Although the embodiment of FIG. 2 illustrates an embodiment in which the width (from the first side 30 to the second side 32) is smaller than the length (from the front end 26 to the back end 28), these dimensions may vary widely. In one embodiment, the length of the body 24 may be approximately 14 inches, the width may be approximately 5½ inches, and the height of the embodiment may be approximately 2¾ inches.

The body 24 may be made of any variety of materials. In one embodiment, the body 24 may be made of a rigid or semi-rigid material, such as a metal, a metallic alloy, or another natural or synthetic material. In another embodiment, the body 24 may be made of a material that does not conduct electricity easily, such as a plastic, so that an electric field applied to one element of the frame 12 will not subject the entire body 24 to such a force.

The frame 12 may contain a handle 34 or some other element that may be used by an operator to grasp the frame 12 with ease. The size of the handle 34 may vary. FIG. 2 illustrates a frame 12 with a handle 34 attached to the body 24 in approximately the middle of an upper surface 36 or top surface of the body 24. The location of the handle 34, however, may vary in different embodiments of the invention.

a. The Rolling Devices

The frame 12 contains at least one support 20 to interface with the tire interior surface so that upon rotation of the tire 5 the frame 12 moves freely relative to the tire interior surface and by gravitational force remains in substantially the lowest portion of the tire interior surface to be tested. The support 20 may be a device 20, such as a rolling device 20, as depicted in the Figures. In other embodiments, the support 20 could be lubrication so that the frame 12 may slide along the tire interior surface or an air support system to keep the frame 12 supported above the tire interior surface. Other supports 20 known to those skilled in the art may also be used within the scope of the invention.

In an embodiment in which the support 20 is a rolling device 20, the frame 12 may contain one or more rolling devices 20. This rolling device 20 or these rolling devices 20 may be either standard disk wheels, as illustrated in FIG. 2, fixed or rotating castors, cambers or other wheels tilted at an angle to the body 24, or any other type of rolling device 20 known to those skilled in the art. The rolling devices 20 may be made of any material known to those skilled in the art, including plastic, rubber, metal, or the like. The dimensions of the rolling device 20 of the invention may also vary within the scope of the invention.

FIG. 2 illustrates an embodiment in which the rolling devices 20 are wheels. The embodiment of FIG. 2 contains four wheels in pairs of two. Each pair of wheels is connected to the body 24 using an axle 38, although the wheels may also be connected directly to the body 24 through other connectors known to those skilled in the art. In one embodiment, the wheels are attached to the body 24 using bearings and shoulder bolts, although screws and ball bearings could be used in other embodiments. In the embodiment illustrated in FIG. 2, the wheels may have a diameter on the order of 2½ to 5 inches, and more particularly, an inner diameter of 3¾ inches and an outer diameter of 3½ inches. The rolling devices 20 of the frame 12 may extend partially beyond the front end 26 of the frame 12, as are the wheels of FIG. 2. In the embodiment of FIG. 2, the wheels near the rear end 28 may also extend beyond the rear end 28, although, as seen in FIG. 2, the wheels may also not extend beyond the rear end 28. Also, in the embodiment of FIG. 2, the wheels extend beyond the top face 36 of the body 24, although this is not necessary. In another embodiment, three or more pairs of wheels may be used as the rolling devices 20 of the invention.

Figure 5:
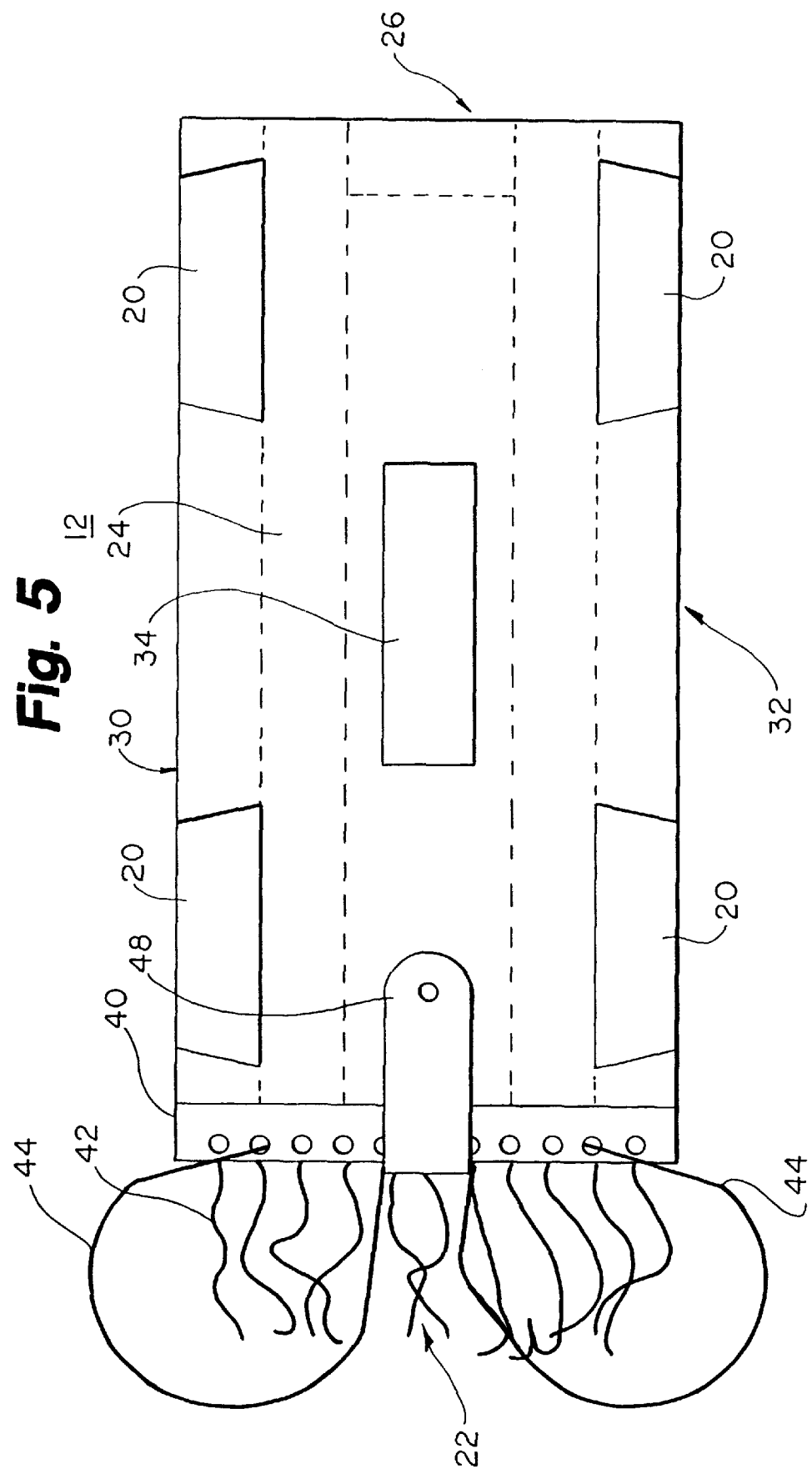
FIG. 5 is a top view of the embodiment of the frame of FIG. 3.

FIG. 3 shows a view of the frame 12 of the invention from the front end 26. The rolling devices 20 in this embodiment, which are wheels, are sunk into the body 24 of the frame 12. In other words, the wheels in this embodiment do not extend beyond the sides 30, 32 of the body 24. In this embodiment, the wheels also do not extend beyond the top face 36 of the body 24. Within the scope of the invention, therefore, a variety of shapes of rolling devices 20, as well as dimensions and orientations with respect to the body 24, may be used. FIG. 4 illustrates a side view of the frame 12 of one embodiment of the invention, and FIG. 5 illustrates a top view of the embodiment of FIG. 4. As can be seen from the embodiment of FIG. 5, the rolling devices 20 may be sunk into the body 24 of the frame 12.

b. The Pins

The frame 12 may contain at least one probe or pin 22 to serve as a carrier of an electric field for use in the invention, as illustrated in FIGS. 2, 4, and 5. The pins 22, therefore, may be electrical conductors. The probe 22 may be either a pin, chain pin, wire, brush, or any conductor that may be used to create an electric field near the surface of the tire 5 to be tested. In one embodiment, the frame 12 contains a plurality of pins 22 connected to the back end 28 of the body 24 or to a runner 40 connected to the back end 28 of the body 24. In another embodiment, all or a portion of the plurality of pins 22 are chain pins 42 as illustrated in FIG. 2. Each chain pin 42 may be made from any suitable electrical conductor and may be of varying length. The length of the chain pins 42, in one embodiment, is sufficiently long to extend proximal to the surface below the frame 12 and, in another embodiment, further than the surface such that the chain pins 42 touch the surface, bend and may partially overlap.

In an embodiment using chain pins 42 as illustrated in FIG. 2, the chain pins 42 may be spaced apart and staggered in a line or rough line from one side 32 to another side 30 of the body 24. The term "chain pins" will be used throughout this specification to refer to any type of wire, chain, or other electrical conductor that may be used to carry an electric potential, and more particularly, to chains that are an electrical conductor. In one embodiment, the chain pins 42 may be spaced at approximately ¼ inch intervals. In other embodiments, this interval may differ. The embodiment of the chain pin 42 layout as shown in FIG. 2, when in use, may produce a sufficient electric field near the interior surface of the tire 5 so that a flaw in any area of the tire 5 may be detected. In particular, the chain pins 42 extend over the bottom surface of the interior of the tire 5 such that they may be used to detect flaws on the tire 5 on the bottom interior surface thereof.

FIG. 2 also illustrates an embodiment in which the pins 22 may include sidewall wires 44. The term "pin," therefore, may refer to a variety of electrical conductors. Throughout this specification, the term "pins" will be used in a general sense to refer to either or both of the sidewall wires 44, the chain pins 42, brushes, wheels, or any other electrical conductors that may be used within the scope of the invention to carry an electric field to near the inside surface of the tire 5. The sidewall wires 44 extend at least partially vertically and partially outward from the body 24 so that the sidewall wires 44 may be used to detect flaws that are located substantially on the side interior surface of the tire 5. While the chain pins 42 may detect flaws on the bottom interior surface of the tire 5, the sidewall wires 44 may partially overlap the surface area covered by the chain pins 42 but will substantially cover the areas of the side of the tire 5 that may be prone to flaws.

c. Connectors for the Pins

A runner 40 may be connected to the back end 28 of the body 24, as seen in FIGS. 2, 4, and 5. This runner 40, which may be made from a variety of materials and may be a variety of sizes, may, in one embodiment, be made from an electrical conductor so that it may be used to carry an electric potential to the pins 22. In another embodiment, the runner 40 could be made from a nonconductive material and then wires or conductive paths on the runner 40 could carry the electric potential to each of the individual pins 22. In the embodiment of FIG. 2, the runner 40, also referred to as a conductive runner in this embodiment, may be a thin metallic rectangular block that is attached lengthwise to the back end 28 of the body 24 at approximately mid-height of the body 24. The runner 40 may be connected to the body 24 using any method known to those skilled in the art, including by adhesive, bolt, screw, or otherwise. The runner 40 may also contain a connection location 46 in which a cord or wire carrying voltage from the voltage generator 18 may be connected. Because, in one embodiment, the runner 40 is made from a conductive material, the electric force carried by the runner 40 will be spread to each of the pins 22 connected to the runner 40.

A rack 48 may also be connected to the body 24. In one embodiment, the rack 48 may extend substantially vertically from the body 24 from a point on the body 24 near the back end 28 thereof. In other embodiments, the rack 48 may extend partially vertically from the body 24. A cord or wire 150 carrying the voltage from the voltage generator 18 may be connected to the body 24 through the rack 48 and thence to pins 22 and sidewall wires 44. In the embodiment of FIG. 2, for instance, the rack 48 may contain suitable connectors of any type known to those skilled in the art to enable the cord or wire 150 from the voltage generator 18 to be easily connected to the rack 48. In addition, the cord or wire 150 from the voltage generator may run through an interior portion of the rack 48 and may then be connected to the runner 40 by any common connector known to those skilled in the art.

In addition to allowing for the connection of the frame 12 to the voltage generator 18, the rack 48 may also be used as a connector for the sidewall wires 44. In the embodiment of FIG. 2, for instance, one end of each sidewall wire 44 is connected to the runner 40 and the other end is connected to the rack 48 at a location that is vertically above the runner 40. As explained above, the sidewall wires 44 may be used to cover the side interior portions of the tire 5 so that flaws in those areas may be detected. In one embodiment, the rack 48 may contain a portion 50 extending partially downward vertically and partially horizontally. This portion 50 may be used for the connection of the sidewall wires 44 to the rack 48. In one embodiment, the portion 50 may contain screws or other devices that are electrical conductors and that may be attached, either directly or indirectly, to the cord or wire from the voltage generator 18. Much like the runner 40, the rack 48 may be made of an electrically conductive material, although in other embodiments it may be made from a material, such as plastic, that is not highly conductive. The size, geometry, and dimensions of the rack 48 may vary. In one embodiment, such as is shown in FIG. 2, the rack 48 is substantially rectangular in shape with the portion 50 extending therefrom. The height of the rack 48 may vary. In the embodiment of FIG. 2, the height of the rack 48, or the distance from the top face 36 of the body 24 to the top of the rack 48, is approximately 8 to 12 inches, or more particularly, 10 inches.

B. Operation and Centering of the Invention

Figure 6:
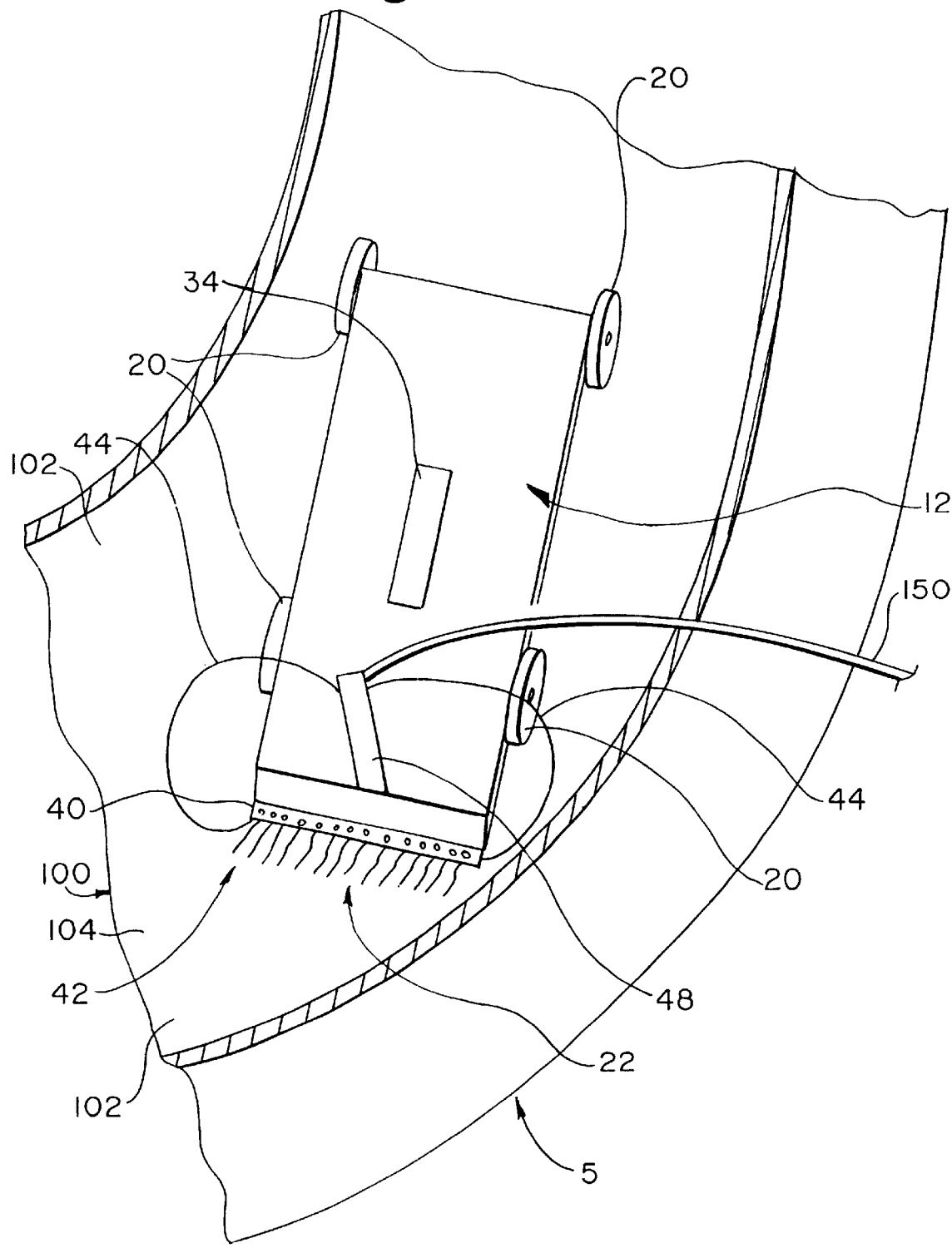
FIG. 6 is a top perspective view of the frame of the invention in the interior of a tire that is to be tested.
Figure 7:
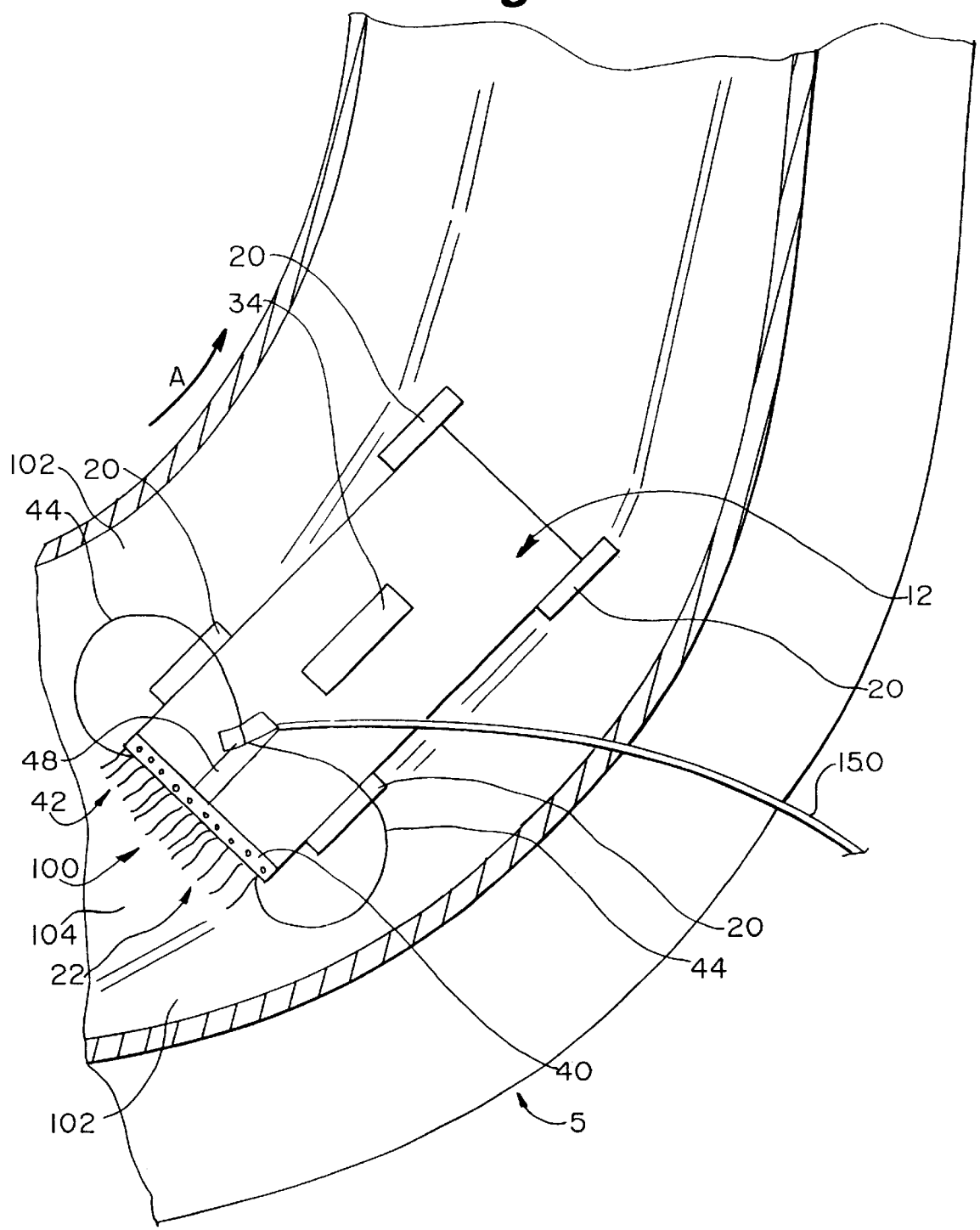
FIG. 7 is a top perspective view of the frame of the invention in the interior of a tire that is to be tested during rotation of the tire.

FIGS. 6 and 7 show one embodiment of the invention in operation. In operation, the frame 12 is placed in the interior 100 of the tire 5 to be tested. As explained above, the tire 5 may be placed on the rotating device, and, optionally, the beads of the tire 5 may be spread apart using the spreader arms 16 (not shown in FIGS. 6 and 7) so that the interior 100 of the tire 5 may be more easily accessed. The voltage generator 18 may be connected to the frame 12 with a cord or wire 150 so as to create an electric field in the pins 22 near the frame 12. When the tire 5 is rotated using the rotating device, the frame 12 rolls on its rolling device 20 so as to remain in substantially the same position within the tire 5 at the bottom of the tire 5. The interior 100 of the tire 5, therefore, moves with respect to the frame 12, such that a given point on the interior surface of the tire 5 will eventually travel in a full circle with respect to the frame 12. In one embodiment, the support 20 of the frame 12 interfaces with the interior 100 of the tire 5 so that upon rotation of the tire the frame 12 moves freely relative to the interior 100 of the tire 5 and by gravitational force remains in substantially the same lowest portion of the interior 100 of the tire 5.

As explained above, the frame 12 may be sized to be placed in the interior 100 of a variety of different sizes of tires 5. The size of the frame 12, therefore, may vary in different embodiments to correspond to the size of the tire 5 to be tested. Wider tires 5, for instance, may be tested better with a frame 12 that is wider than a frame 12 designed for a tire 5 of smaller width.

FIG. 6 shows the tire tester 10 of the invention in operation at the beginning of a testing session. The frame 12 is placed in the interior 100 of the tire 5. The interior 100 of the tire 5 may contain a bottom surface 104 which may be continuously connected to side interior surfaces 102 of the tire 5. Although these side surfaces 102 of the interior 100 of the tire 5 are referred to as separate surfaces, they may be one continuous surface with the bottom surface 104. The bottom surface 104 may be substantially flat, but it may also be somewhat rounded. Upon rotation of the tire 5, the frame 12 travels around the interior 100 of the tire 5 on either the bottom surface 104 or partially on the bottom surface 104 and partially on the side interior surfaces 102.

When the frame 12 is first placed in the interior 100 of the tire 5, it may be somewhat out of alignment, as seen in FIG. 6. It is desirable to have the frame 12 aligned in both a circumferential and in a radial orientation in the tire 5. For instance, it may be desirable to have the frame 12 centered as much as possible on the bottom surface 104 of the tire 5. The reason this centering may be desirable is to keep the pins 22 in the proper location on the interior 100 of the tire 5 so that flaws in the tire 5 may be detected. The chain pins 42, for instance, may function better if they extend primarily on the bottom surface 104 of the tire 5 and if they cover as much of the bottom surface 104 of the tire 5 as possible. Similarly, the sidewall wires 44 may function better if they are properly aligned in the tire 5 so that they extend and cover each of the side interior surfaces 102 of the tire 5. If the frame 12 is out of alignment in the tire 5, the sidewall wires 44 may be out of alignment—i.e., one of the sidewall wires 44 may not extend close enough to the side interior surface 102 of the tire 5 so that an electric field near the surface of the tire 5 is created. For a number of reasons that may affect the performance of the tire tester 10 of the invention, it may be desirable to have the frame 12 centered within the interior 100 of the tire 5 so that an electric force carried by the pins 22 is directed to the entire surface of the interior 100 of the tire 5 that is to be tested for flaws.

FIG. 7 shows the frame 12 of the invention centered in the interior 100 of the tire 5 when the tire 5 is rotated in the direction of arrow A. Upon rotation of the tire 5, the frame 12 may move about in the interior 100 of the tire 5 until it reaches a steady equilibrium in a centered position in the tire 5. The frame 12, therefore, may be self-centering in the tire 5 upon rotation of the tire 5 without further human intervention. It should be noted that the effect of gravity holds the frame 12 in the bottom portion of the tire 5 as it rotates. Furthermore, the side surfaces 102 of the tire 5 itself hold the frame 12 laterally within the tire 5 and help to align the frame 12 upon rotation of the tire 5.

A variety of designs of the frame 12 may allow for self-centering upon rotation of the tire 5 to be tested. Some such embodiments of frames 12 that may be self-centering are the embodiments shown in FIGS. 2–7. In these embodiments, four wheels are attached to a rectangular body 24. Upon rotation of the tire 5 in these embodiments, which have been described throughout this specification, the frame 12 may be efficient at quickly self-centering within the interior 100 of the tire 5. In the embodiment shown in FIG. 7, the wheels (rolling devices 20) may be attached to the body 24 so that the wheels do not turn with respect to the body 24. Upon rotation of the tire 5 for this embodiment, however, the frame 12 self-centers within the tire 5 as shown in FIG. 7. In other embodiments, the wheels may be connected to the body 24 such that the wheels turn with respect to the body 24. In yet other embodiments, such as those using fewer than four wheels or using cambers or casters instead of wheels, the frame 12 may also function to allow for self-centering within the tire 5 without human intervention.

Although the frame 12 may self-center in the tire 5 passively in some embodiments, the frame 12 may also include a motor and pendulum or a servo, referred to together with numeral 50 in FIG. 2, that may aid in actively centering the frame 12 within the tire 5 during rotation. For instance, a pendulum may sense that the frame 12 is too far toward either one of the side interior surfaces 102 of the tire 5. The pendulum may then send a signal to the motor such that the motor controls one or more rolling devices 20, such as the wheels of FIG. 2, to center the frame 12 within the tire 5. Such a pendulum may also work if the frame 12 is, for some reason, too far forward or rearward in the tire 5. In such a situation, the motor may provide a brake to one or more rolling devices 20 or accelerate the rolling device 20 so that the frame 12 may be centered in the tire 5 in the forward/rearward direction. The motor of such a self-centering system may be powered by a battery or, in another embodiment, by the cord 150 that provides the electric potential to the pins 22. Any variety of motors, pendulums, or other sensor actuation configurations may be used within the scope of the invention to aid in the self-centering of the frame 12 within a tire 5 to be tested. It should be noted, however, that some embodiments of the frame 12 of the invention function to self-center without the aid of such a motor and pendulum system.

The tire tester 10 of the invention provides numerous advantages over the prior art. One common prior art tire tester, such as that disclosed in U.S. Pat. No. 4,520,307 described above, may require a mechanical or pneumatic arm to correctly place and center the head within the tire 5 to be tested. As explained above, alignment and centering of the head within the tire 5 to be tested is desirable to ensure proper coverage and hence testing of the surface of the tire 5. The frame 12 of the invention may, as explained above, be self-centering within the tire 5 upon rotation of the tire 5. Thus, a user does not have to spend the time and energy to properly align the head within the tire 5 using a mechanical or pneumatic arm to ensure proper testing of the tire 5 for flaws. An advantage of the invention, therefore, is that it may save the user significant amounts of time during use. In addition, the frame 12 of the invention may be easier to use than prior art tire testers.

Yet another benefit of the frame 12 of the present invention over the prior art is that it is less complex than a tire tester that contains a pneumatic or mechanical arm to place the head within the tire 5 for testing. The frame 12 of the invention, therefore, may be less costly, and perhaps significantly less costly to construct or buy because few and less expensive parts may be used. Because the frame 12 of the present invention may be less complex, it may take up less space in storage or in use. The invention, therefore, provides benefits with respect to decreased cost and complexity and increased ease of use. At the same time, the invention may provide all of the benefits of the prior art tire testers in terms of functionality, such as detecting flaws either visually or electronically as explained above.

The invention may also be sold and used independently of a specific tire spreader. In fact, a tire spreader is not even required for the invention. A user could simply rotate the tire manually to use the invention. Because the invention does not contain a complex mechanical or pneumatic arm that must be designed for a specific tire spreader, the invention may be used with any tire spreader or, as stated above, without a tire spreader. The invention, therefore, may significantly reduce the costs of a tire testing system.

In another embodiment, the invention may be a method for detecting flaws in a tire 5. In this embodiment, the frame 12 may be placed in the interior 100 of the tire 5 to be tested. An electric potential may then be applied to the interior 100 or inside of the tire 5 through the pins 22 of the frame 12. Such an electric potential or field may be supplied through a cord 150 from the voltage generator 18 to the frame 12. The tire 5 may then be rotated so that the frame 12 rotates on the at least one roller 20. Upon detection of a flaw, an electric arc may be produced. Such an electric arc indicates a flow of current through the pins 22 to a reference, such as the rollers 14 shown in FIG. 1. In connection with this embodiment of the invention, the rotation of the tire 5 may be automatically stopped upon the detection of a flaw in the tire 5 by the current meter 19 so that the flaw may be marked for mending in the future.

While the present invention has been described with reference to several embodiments thereof, those skilled in the art will recognize various changes that may be made without departing from the spirit and scope of the claimed invention. Accordingly, this invention is not limited to what is shown in the drawings and described in the specification but only as indicated in the appended claims.

What is claimed is:

1. A voltage applicator for tire inspection comprising:
   a body;
   means for supporting the body upon a first portion of tire surface and allowing movement of the body from the first portion of tire surface to a second portion of tire surface;
   conductive means, carried by the body, for distributing an electric field over a surface of tire to be inspected.

2. The voltage applicator of claim 1 and wherein the first portion of tire surface and the second portion of tire surface are interior surfaces.

3. The voltage applicator of claim 1 and wherein the surface of tire to be inspected is an interior surface.

4. The voltage applicator of claim 1 and wherein the means for support and allowing movement are selected from the group consisting of wheels, lubrication, and air support.

5. The voltage applicator of claim 1 and wherein the means for supporting and allowing movement include at least one wheel supporting the body and the at least one wheel is selected from the group consisting of castor wheel, camber wheel, and disk wheel and the at least one wheel is made from a material selected from the group consisting of plastic, rubber, and metal.

6. The voltage applicator of claim 1 and wherein the means for supporting and allowing movement are responsive to gravity in maintaining support upon the tire surface and allowing movement from the first portion of tire surface to the second portion of tire surface.

7. The voltage applicator of claim 1 and wherein the conductive means, carried by the body, for distributing an electric field over a surface of tire to be inspected are selected from the group consisting of pin, chain pin, wire, and brush.

8. The voltage applicator of claim 1 and wherein the conductive means, carried by the body, for distributing an electric field over a surface of tire to be inspected are a plurality of pins, chain pins, wires, or brushes.

9. The voltage applicator of claim 1 and further including:
   means for aligning, relative to a third tire surface, during movement of the body from the first portion of tire surface to a second portion of tire surface.

10. The voltage applicator of claim 9 and wherein the first and second tire surfaces are interior tire surfaces and the third surface is an interior tire sidewall surface.

11. The voltage applicator of claim 9 and wherein the means for supporting and allowing movement include at least two wheels and the means for aligning include selective braking applied to one of the at least two wheels.

12. The voltage applicator of claim 9 and wherein the means for supporting and allowing movement include at least two wheels and the means for aligning include selective acceleration applied to one of the at least two wheels.

13. The voltage applicator of claim 9 and wherein the means for supporting and allowing movement include at least two wheels and the means for aligning include selective steering applied to one of the at least two wheels.

14. The voltage applicator of claim 1 and further including:
means for self-centering, relative to a third tire surface and a forth tire surface, during movement of the body from the first portion of tire surface to a second portion of tire surface.

15. The voltage applicator of claim 14 and wherein the first and second tire surfaces are interior tire surfaces, the third surface is an interior tire sidewall surface and the fourth surface is an opposing interior tire sidewall surface.

16. The voltage applicator of claim 14 and wherein the means for supporting and allowing movement include at least two wheels and the means for aligning include selective braking applied to one of the at least two wheels.

17. The voltage applicator of claim 14 and wherein the means for supporting and allowing movement include at least two wheels and the means for aligning include selective acceleration applied to one of the at least two wheels.

18. The voltage applicator of claim 14 and wherein the means for supporting and allowing movement include at least two wheels and the means for aligning include selective steering applied to one of the at least two wheels.

19. The voltage applicator of claim 1 and further comprising:
an electric power source, and wherein the power of the power source is employed by the voltage applicator.

20. The voltage applicator of claim 19 and wherein the power is employed to operate a motor.

21. The voltage applicator of claim 19 and wherein the power is employed to operate a brake.

22. The voltage applicator of claim 19 and wherein the power source is remote from the body and transmitted through a cord to the voltage applicator.

23. The voltage applicator of claim 19 and in which the power source is resident in a battery carried by the body.

24. The voltage applicator of claim 1 and wherein the voltage applicator is sized to allow insertion between the beads of a tire to be tested and placement upon a portion of interior tire surface, so as to allow movement within the tire without further human intervention.

25. A method of culling a defective tire carcass from a group of tire carcasses to facilitate repair of defects prior to buffing and retreading of the defective tire carcass, comprising the steps of:
providing a voltage applicator having a body, means for supporting the body upon a first tire carcass surface and allowing movement of the body from the first tire carcass surface to a second tire carcass surface, and conductive means, carried by the body, for distributing an electric field over a surface of tire carcass to be inspected;

orienting a tire carcass of the group of tire carcasses on a substantially horizontal axis;

inserting the voltage applicator between beads of the oriented tire carcass and then placing the inserted voltage applicator upon an inner surface of the tire carcass;

supplying voltage to the conductive means of the voltage applicator whilst simultaneously rotating the oriented tire carcass and allowing the voltage applicator to move along the inner surface of the tire carcass;

providing a conductor adjacent an exterior surface of the oriented, rotating tire carcass and adjacent the moving voltage applicator, such that the rotating tire carcass is interposed between the conductor and the moving voltage applicator, culling a tire carcass which allows an arc of current between the moving voltage applicator and the external conductor.

* * * * *